United States Patent
Alexander et al.

(10) Patent No.: US 7,224,447 B2
(45) Date of Patent: May 29, 2007

(54) SYSTEM AND METHOD FOR MEASURING THE PERMEABILITY OF A MATERIAL

(75) Inventors: Bogdan N. Alexander, Richmond, VA (US); Kenneth E. Rudolph, Jr., Louisville, KY (US); Ronald Ölschläger, Tangstedt (DE); Tino Häupke, Hamburg (DE)

(73) Assignee: Philip Morris USA Inc., Richmond, VA (US)

( * ) Notice: Subject to any disclaimer, the term of this patent is extended or adjusted under 35 U.S.C. 154(b) by 303 days.

(21) Appl. No.: 10/854,338

(22) Filed: May 26, 2004

(65) Prior Publication Data

US 2005/0195411 A1    Sep. 8, 2005

Related U.S. Application Data

(60) Provisional application No. 60/551,455, filed on Mar. 8, 2004.

(51) Int. Cl.
*G01N 21/00* (2006.01)

(52) U.S. Cl. .................. 356/238.1; 356/238.2

(58) Field of Classification Search ............... 356/402, 356/429, 430, 431, 626, 238.1, 238.2, 364; 250/548; 396/647, 612
See application file for complete search history.

(56) References Cited

U.S. PATENT DOCUMENTS

| | | | |
|---|---|---|---|
| 2,528,158 A | 10/1950 | Menke | |
| 3,361,029 A * | 1/1968 | Russell et al. | 356/444 |
| 4,025,752 A | 5/1977 | Whitman, III | |
| 4,205,769 A | 6/1980 | Blitchington | |
| 4,218,606 A | 8/1980 | Whitman, III | |
| 4,219,727 A | 8/1980 | Bolt | |
| 4,224,497 A | 9/1980 | Duley et al. | |
| 4,224,498 A | 9/1980 | Grollimund et al. | |
| 4,246,775 A | 1/1981 | Stultz | |
| 4,247,754 A | 1/1981 | Baier | |
| 4,265,254 A | 5/1981 | Koch et al. | |
| 4,281,670 A | 8/1981 | Heitmann et al. | |
| 4,297,559 A | 10/1981 | Whitman, III | |
| 4,383,435 A | 5/1983 | Hinzmann | |
| 4,390,032 A | 6/1983 | Labbe et al. | |
| 4,410,785 A | 10/1983 | Lilly, Jr. et al. | |
| 4,439,663 A | 3/1984 | Lilly, Jr. et al. | |
| 4,501,953 A | 2/1985 | Hollinetz et al. | |

(Continued)

FOREIGN PATENT DOCUMENTS

DE    43 02 137    6/1993

(Continued)

*Primary Examiner*—Hoa Pham
*Assistant Examiner*—Tri Ton
(74) *Attorney, Agent, or Firm*—Connolly Bove Lodge & Hutz LLP

(57) ABSTRACT

A system for measuring the permeability of a material includes a light source for illuminating the material, and a stray light sensor for detecting stray light traveling through the material from the light source and outputting a stray light signal indicative of the stray light detected. The system further includes a direct light sensor for detecting direct light traveling through holes in the material from the light source and outputting a direct light signal indicative of the direct light detected. Finally, the system includes a digital processing device for receiving the stray light and direct light signals and calculating the permeability of the material.

46 Claims, 12 Drawing Sheets

U.S. PATENT DOCUMENTS

| | | |
|---|---|---|
| 4,537,206 A | 8/1985 | Lorenzen et al. |
| 4,569,359 A | 2/1986 | Nowers et al. |
| 4,916,272 A | 4/1990 | Okumoto et al. |
| 5,092,350 A | 3/1992 | Arthur et al. |
| 5,341,824 A * | 8/1994 | Fletcher et al. ............. 131/281 |
| 5,367,144 A | 11/1994 | Matsumura et al. |
| 5,404,889 A | 4/1995 | Belvederi et al. |
| 6,025,572 A | 2/2000 | Imai et al. |
| 6,049,057 A | 4/2000 | Imai et al. |
| 6,403,966 B1 * | 6/2002 | Oka ........................... 250/372 |
| 2003/0137647 A1 * | 7/2003 | Hasson et al. ............. 356/5.01 |

FOREIGN PATENT DOCUMENTS

| | | |
|---|---|---|
| DE | 44 21 962 | 1/1996 |
| DE | 196 16 018 | 10/1996 |
| DE | 102 51 610 | 5/2004 |
| EP | 0 056 223 | 7/1982 |
| FR | 2 416 461 | 8/1979 |
| GB | 1 588 980 | 5/1981 |
| GB | 1 604 467 | 12/1981 |

* cited by examiner

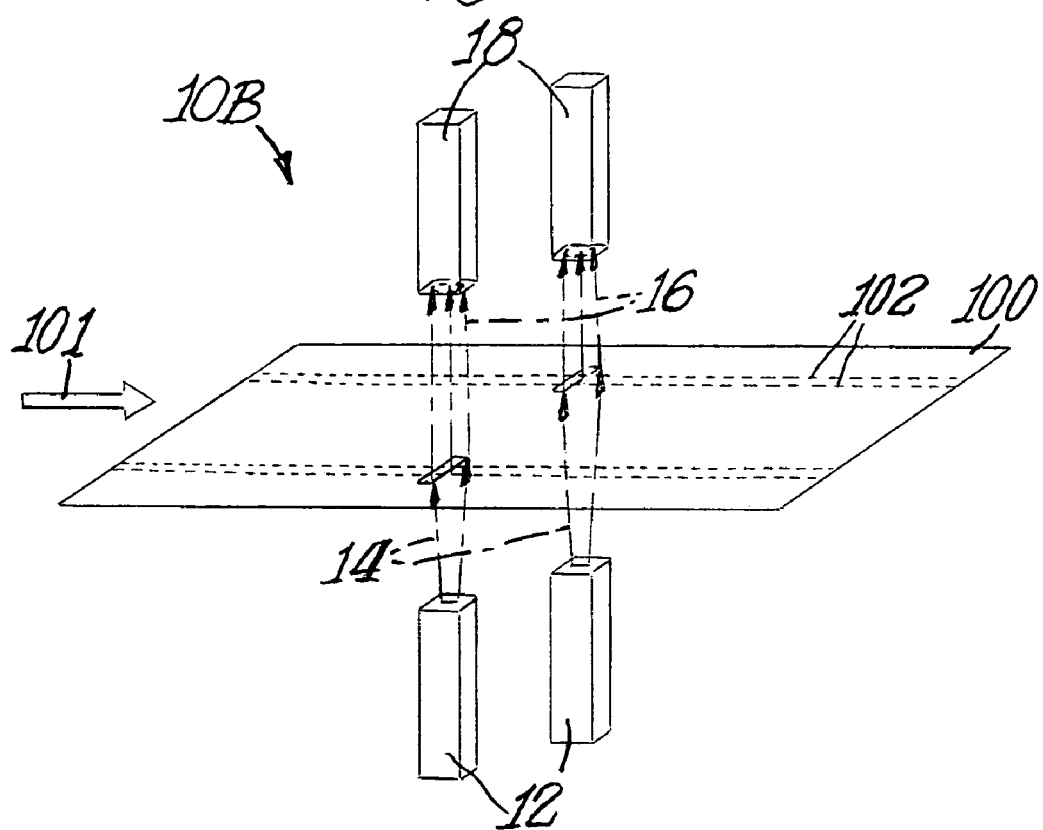

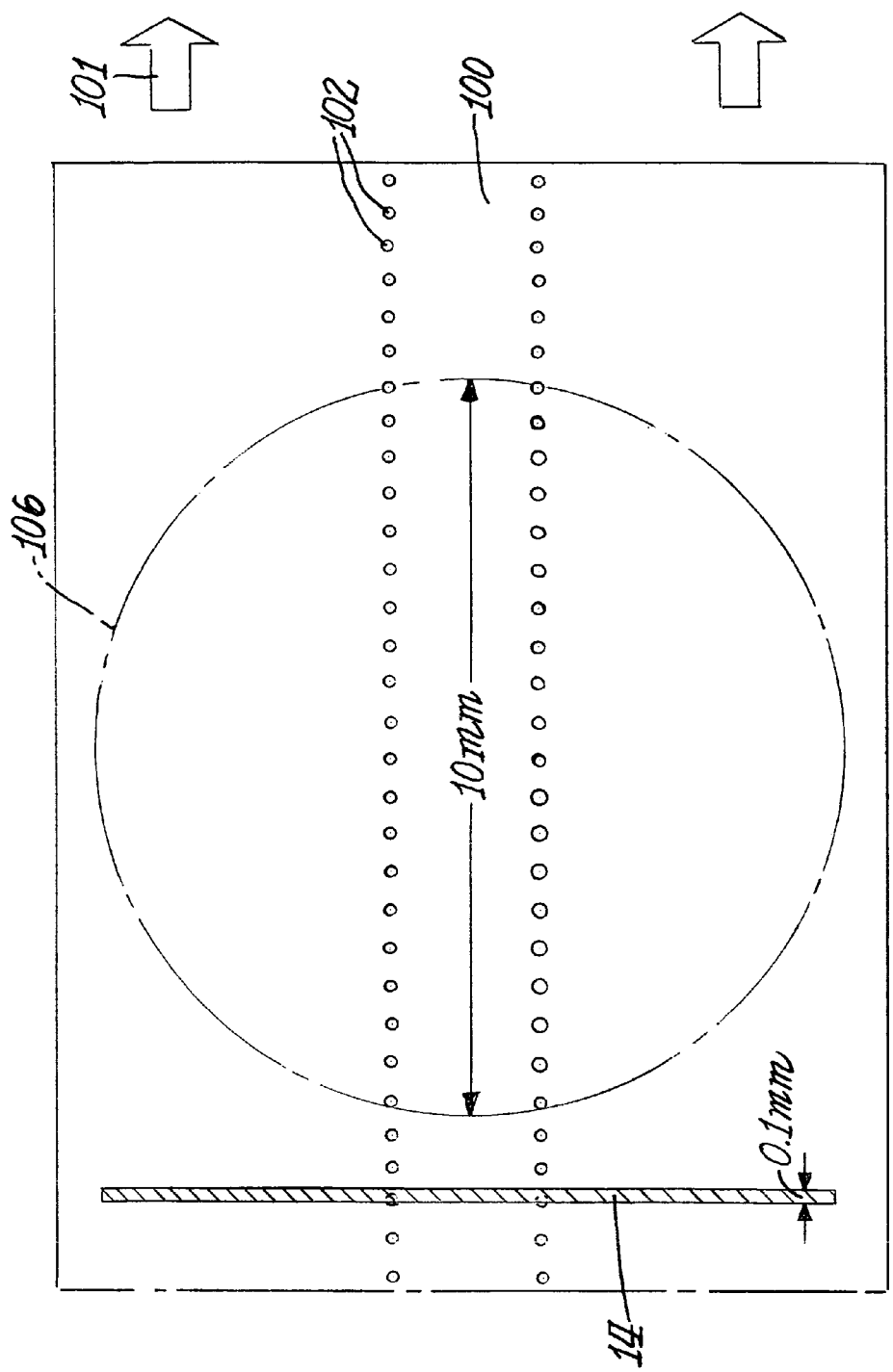

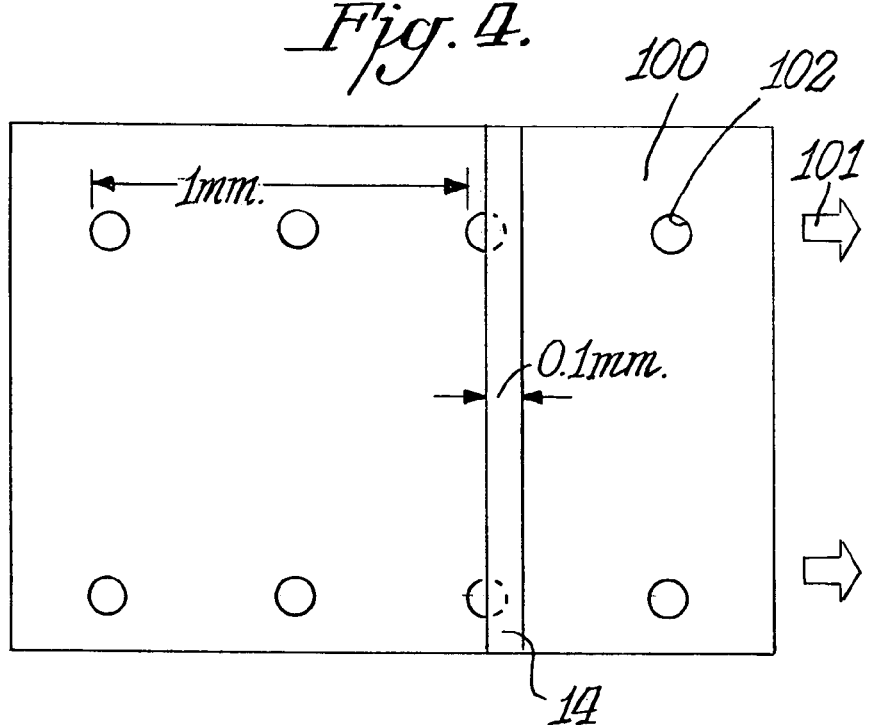
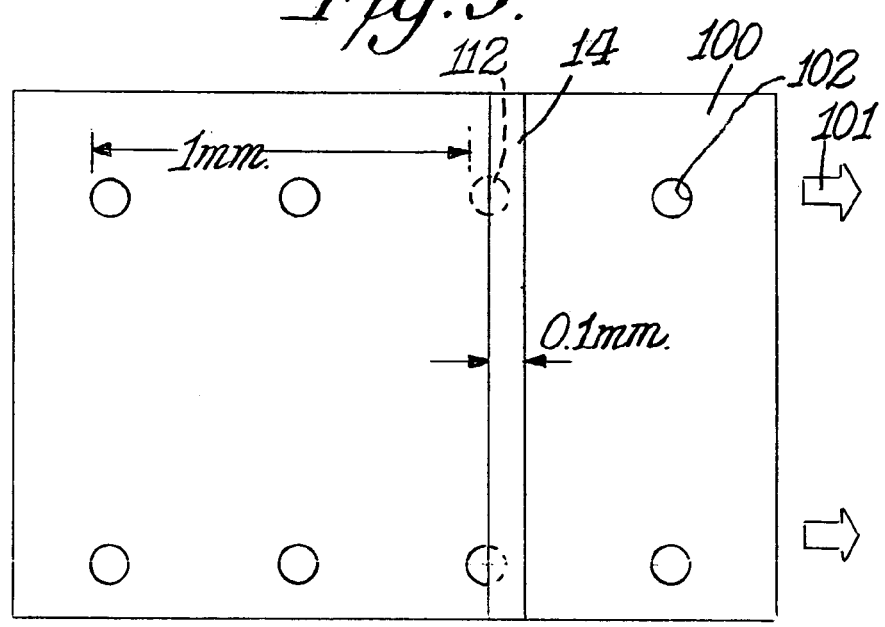

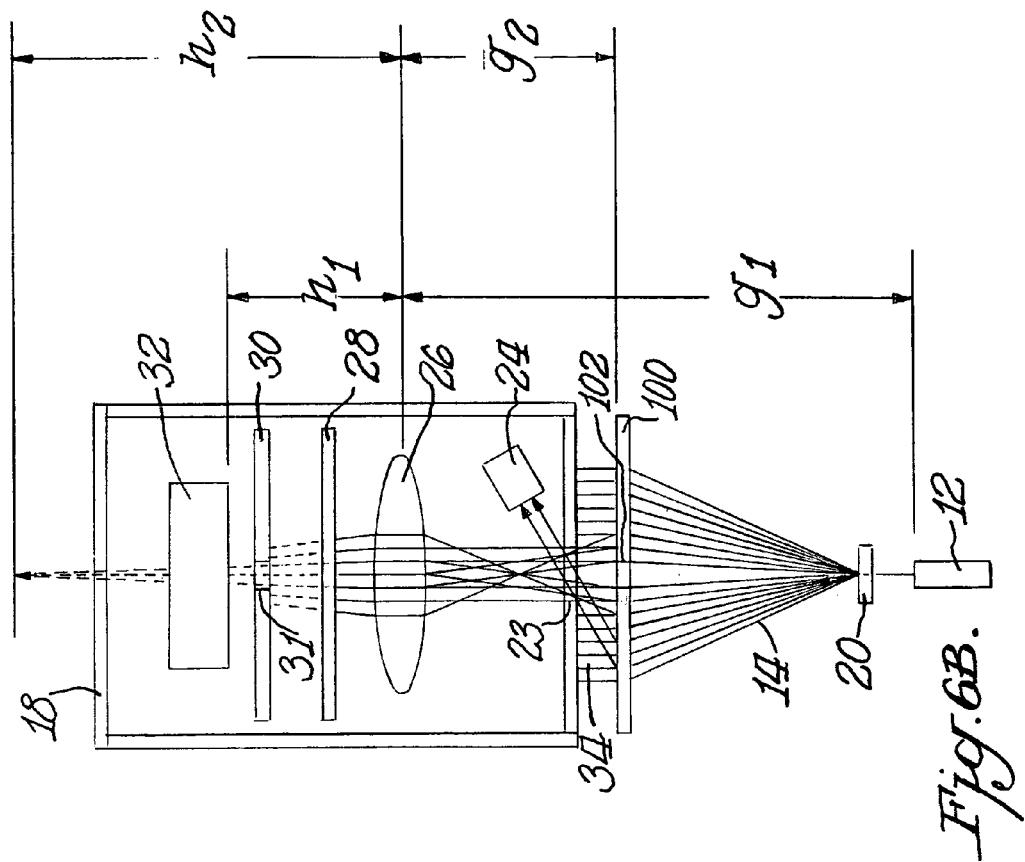
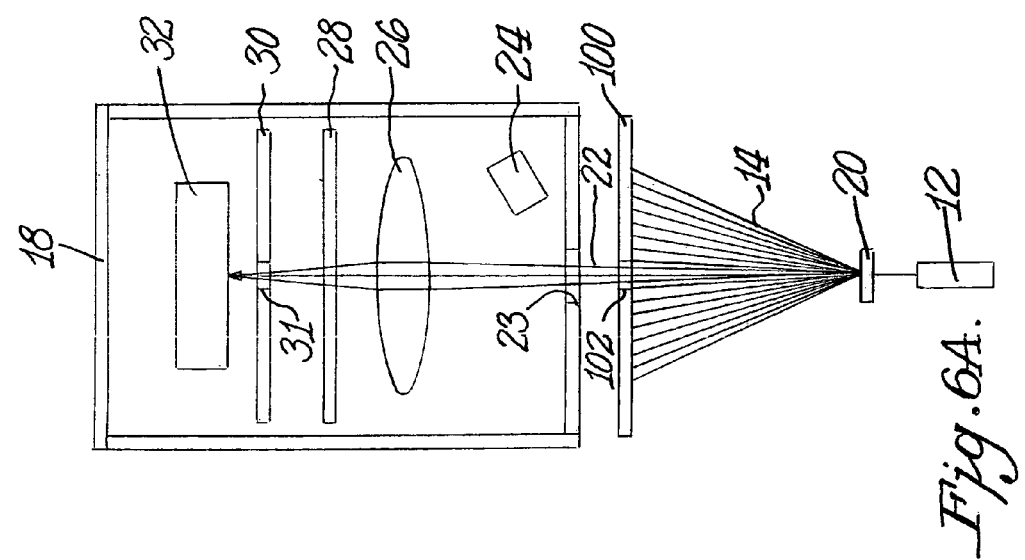
Fig. 6B.
Fig. 6A.

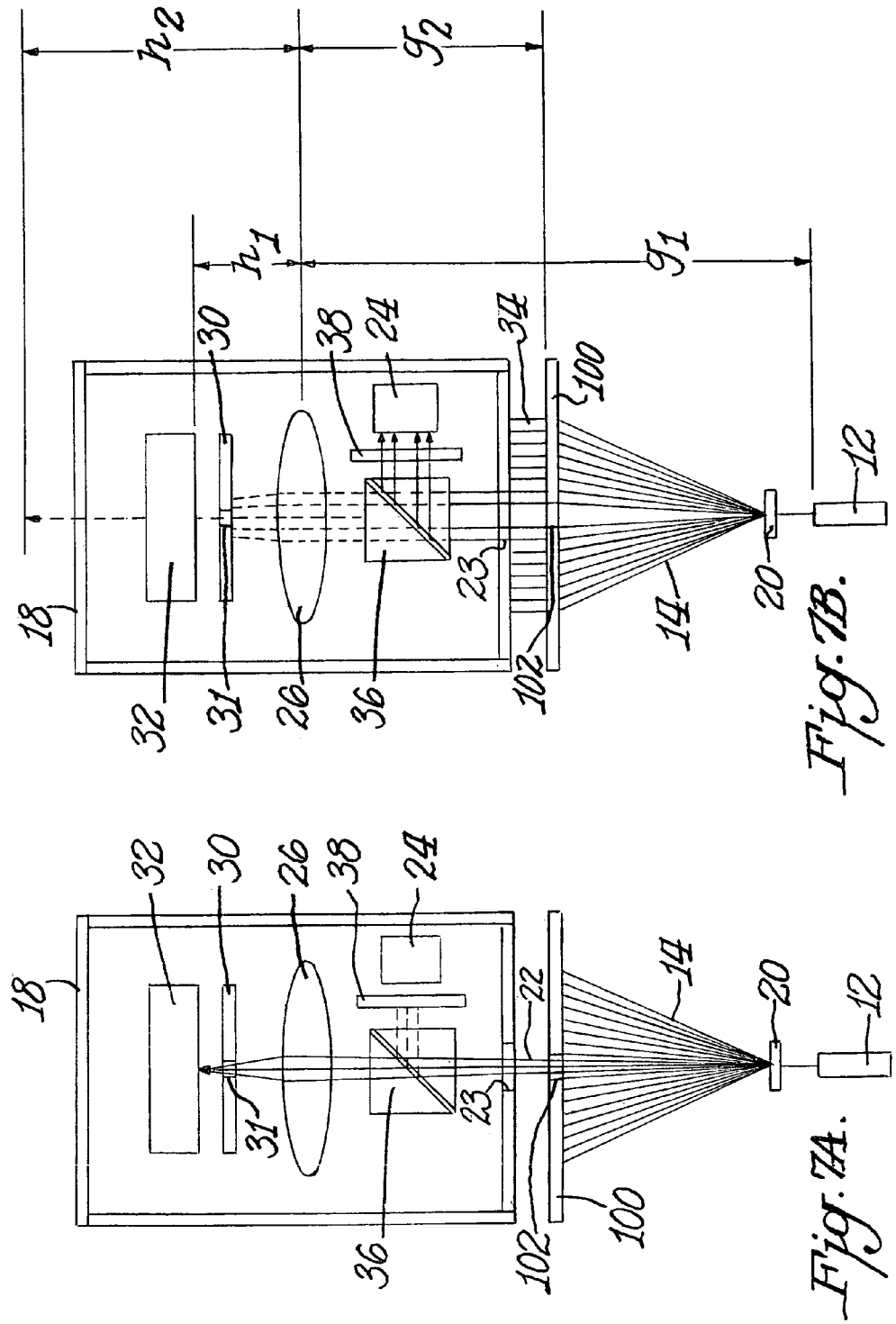

SYSTEM AND METHOD FOR MEASURING THE PERMEABILITY OF A MATERIAL

CLAIM FOR PRIORITY

The present application claims priority of U.S. Provisional Patent Application Ser. No. 60/551,455, filed Mar. 8, 2004, the disclosure of which being incorporated by reference herein in its entirety.

BACKGROUND OF THE INVENTION

A. Field of the Invention

The present invention relates generally to instruments for measuring the permeability of a material, and, more particularly to system and method for measuring the permeability of a material.

B. Description of the Related Art

Many products or materials are provided with holes or perforations. Such products and materials require their permeability to be measured. Examples of such products and materials needing permeability measurements include: wallpaper; filters used for air, chemicals, etc.; materials affording the appropriate degree of liquid (ink, varnish, sizing) absorption in printing; porous bags and materials used in food packaging and agricultural fumigation; insulating materials; paper; textiles; etc.

One particular material provided with such holes or perforations are the wrappers of filter cigarettes or similar rod-shaped tobacco products. The perforations allow cool atmospheric air to enter the column of tobacco smoke. Such wrappers are called tipping paper. Running webs of tipping paper making up rod-shaped tobacco products may be perforated mechanically, electrically, or optically. For example, British Patent No. 1,588,980 discloses a perforating unit that employs a set of needles or analogous mechanical perforating tools that puncture selected portions of the running web. U.S. Pat. No. 2,528,158 and British Patent No. 1,604,467 disclose electro-perforating tools that employ heat-generating electrodes that combust selected portions of the running web. An optical perforating tool, as disclosed in U.S. Pat. No. 4,265,254, uses coherent radiation from a laser to make perforations of a desired size and with a high degree of reproducibility.

Conventional filter-tipped tobacco products are perforated in the region of their filter plugs to insure that atmospheric air can enter the column of tobacco smoke irrespective of the length of combusted portion of the tobacco-containing section of the product. It is desirable to regulate the permeability of wrappers of all articles of a given tobacco product in such a way that the permeability is consistent or deviates only negligibly from a predetermined value.

It is known to control perforations of tipping paper in response to permeability measurements, as discussed in U.S. Pat. Nos. 4,569,359, 4,121,595, 4,648,412 and 5,092,350. Known permeability measuring devices include pneumatic systems for measuring the pressure drop through the tipping paper. However, such pneumatic systems are frequently inaccurate and difficult to implement in a high volume production line where the web can travel through the perforator at speeds of 5000 to 6000 feet per minute.

Pneumatic measurements are frequently made off-line on a sample basis. In some conventional production lines, quality monitoring and control are accomplished through a combination of sampling and perforator adjustments. Initial setup can be accomplished by iterative trial and error in which the focus and power settings of the laser perforator are adjusted. After making tentative settings, the line is run to generate samples. The resulting samples are then tested in a pneumatic pressure drop instrument gauge. Once the desired operating results are achieved, a manufacturing inspector periodically samples the perforated product, for example, a sample could be taken of five foot sections of paper from the end of every third bobbin (or of every bobbin) to check for correct pressure drop. The paper could also be inspected by visual monitoring by holding the paper up to light to check generally for hole position and size. However, since such measurements are neither continuous nor in real time, defective perforation, if detected at all, would be determined after a large quantity of tipping paper has been perforated.

Optical monitoring devices for tipping paper perforation lines are also known, as discussed in U.S. Pat. Nos. 4,569,359 and 5,341,824. A conventional optical system for monitoring a perforation line is illustrated in FIG. 1 and described below. While such a system permits on-line monitoring of the process, in practice the output signal from this system has been found to correlate poorly with the pressure drops measured directly with pneumatic systems. Moreover, the system is affected by variations in the paper base sheet such as splices, extraneous holes, or thickness changes.

As shown in FIG. 1, the conventional optical monitoring system for monitoring perforations 102 in tipping paper 100 (traveling in direction 101) includes a light or optical source or sources 104 that shines a large circular area of light 106 onto the tipping paper 100. Typically, light source 104 is a halogen-based light source. Light 108 emanating through perforations 102 is received by a light or optical detector or detectors 110, and used to monitor and/or control the quality of the perforations 102 in tipping paper 100. The problem with such a conventional arrangement, as best shown in FIG. 3, is that the large circular area of light 106 has a diameter of about ten millimeters (mm) and illuminates an area having a number of perforations 102. Thus, the fine scanning and resolution capabilities of the conventional optical monitoring system are poor, reducing the reliability and accuracy of such a system.

Thus, there is a need in the art to provide a system and method for measuring the permeability of a material such as tipping paper that overcomes the problems of the related art.

SUMMARY OF THE INVENTION

The present invention solves the problems of the related art by providing a system and method for measuring the permeability of a material such as tipping paper.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description. It is to be understood that both the foregoing general description and the following detailed description are exemplary and explanatory only and are not restrictive of the invention, as claimed.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIG. 2B is a schematic elevational view showing a light permeability measuring system in accordance with another aspect of the present invention;

FIG. 3 is a top plan view of a tipping paper being scanned with the conventional light permeability measuring system shown in FIG. 1, and with the light permeability measuring system of the present invention as shown in FIGS. 2A and 2B;

FIG. 4 is a partial top plan view of a section of the tipping paper shown in FIGS. 2A and 2B and showing the narrow line of light of the system of the present invention;

FIG. 5 is a partial top plan view of a section of the tipping paper shown in FIGS. 2A and 2B and showing the narrow line of light of the system of the present invention, wherein the tipping paper is missing one perforation;

FIG. 6A is a schematic side view, partially in section, of the system shown in FIGS. 2A and 2B and showing a light detector with an angled stray light sensor and further showing how direct light enters the light detector;

FIG. 6B is a schematic side view, partially in section, of the system shown in FIGS. 2A and 2B and showing a light detector with an angled stray light sensor and further showing how stray light enters the light detector;

FIG. 7A is a schematic side view, partially in section, of the system shown in FIGS. 2A and 2B and showing a light detector with a beam splitter and a straight stray light sensor and further showing how direct light enters the light detector;

FIG. 7B is a schematic side view, partially in section, of the system shown in FIGS. 2A and 2B and showing a light detector with a beam splitter and a straight stray light sensor and further showing how stray light enters the light detector;

DETAILED DESCRIPTION OF THE PRESENT INVENTION

The following detailed description of the invention refers to the accompanying drawings. The same reference numbers in different drawings identify the same or similar elements. Also, the following detailed description does not limit the invention. Instead, the scope of the invention is defined by the appended claims and equivalents thereof.

Figure 2A:
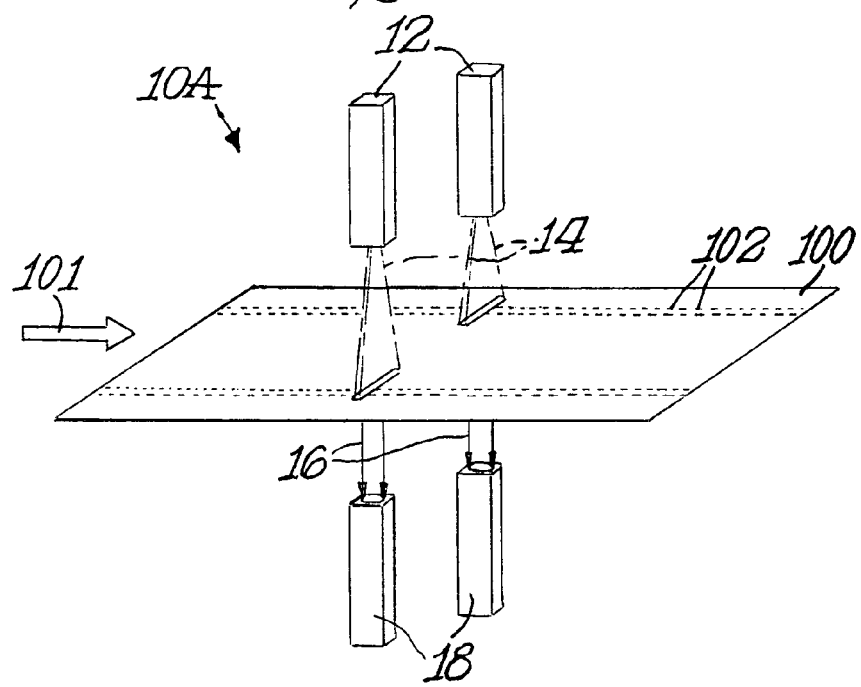
FIG. 2A is a schematic elevational view showing a light permeability measuring system in accordance with an aspect of the present invention.

A system for measuring the permeability of a material in accordance with an aspect of the present invention is shown generally as reference numeral 10A in FIG. 2A and reference numeral 10B in FIG. 2B. FIG. 2A shows an arrangement where light sources 12 are provided above a tipping paper 100, and light detectors 18 are provided below tipping paper 100. Alternatively, as shown in FIG. 2B, light sources 12 may be provided below tipping paper 100 and light detectors 18 may be provided above tipping paper 100. The alternative arrangement of FIG. 2B adds a supplemental protection of light detectors 18 from the environmental light, which in most cases comes from the ceiling and can generate an error signal.

As used herein, the term "material" includes, but is not limited to, products or materials with holes or perforations that require their permeability to be measured. Examples of such products and materials needing permeability measurements include: wallpaper; filters used for air, chemicals, etc.; materials affording the appropriate degree of liquid (ink, varnish, sizing) absorption in printing; porous bags and materials used in food packaging and agricultural fumigation; insulating materials; paper; textiles; wrappers of filter cigarettes or similar rod-shaped tobacco products; etc.

A. System Overview

System 10A or 10B includes light-based permeability measuring instruments, such as, for example, a light or laser source or sources 12 and an optical or light sensor or sensors (detectors) 18. FIGS. 2A and 2B show two light sources 12 and two light sensors 18 for use with tipping paper 100, because tipping paper 100 typically includes two sets of rows of perforations 102. However, system 10A or 10B is not limited to this number of light sources 12 and light sensors 18, and may include more or less than two light sources 12 and two light sensors 18, depending upon the application of system 10A or 10B. As shown in FIGS. 2A and 2B, light sources 12 produce narrow lines of light 14 that illuminate tipping paper 100 and, a portion of which, extends through and emanates from perforations 102 as light beams 16 which are eventually received by light sensors 18. As discussed more fully below with reference to FIG. 12, light sensors 18 may convert the optical data received from light beams 16 into electrical data that may be used to determine the propriety of the quality of perforations 102.

B. Types Of Light Sources

Figure 1:
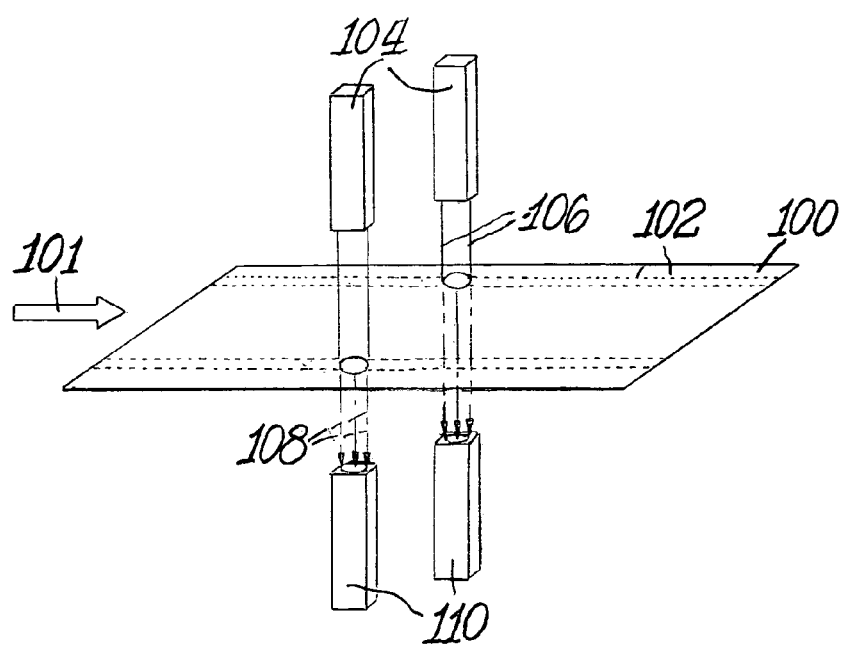
FIG. 1 is a schematic elevational view showing a conventional light permeability measuring system.

Preferably, light source 12 is a polarized light source (such as a laser) instead of the traditional non-polarized light source (usually a high-intensity halogen light) used in conventional optical monitoring systems, as shown in FIG. 1. With a polarized light source 12, light traveling through perforations 102, hereinafter referred to as "direct light", remains polarized, while the light penetrating through the non-perforated areas of tipping paper 100, hereinafter referred to as "stray light", changes its polarization characteristics. This makes it possible to distinguish between direct light and stray light, as discussed more fully below with reference to FIGS. 6A, 6B, 7A, and 7B.

Use of a laser for light source 12 provides a coherent, modulated or non-modulated light source with which to scan the material (e.g., tipping paper 100). Coherent light properties, such as monochromaticity and low divergence, increase the performance of the optical configuration of system 10A or 10B. Other advantages of using a laser for light source 12 instead of a conventional halogen-based light source include: increased life (a laser has one order of magnitude more life than a halogen light); lower power requirements for the laser; smaller size of the laser; etc.

The wavelength of the laser used as light source 12 in system 10A or 10B may be in general in the red light spectrum (e.g., approximately 660 nanometers(nm)). However, a violet or ultra-violet laser light source may be used instead of, or preferably in combination with, the red laser light source. A light with a wavelength as low as 405 nm (violet light), or even as low as 350 nm (ultra-violet light), helps to reduce the stray light component, eliminating the differences between tipping papers having different colors (for example, tipping papers typically come in white, cork, and cork-on-white colors). However, currently, violet and ultra-violet light lasers are not the preferred choice for light source 12 because of their larger size and higher price than red light lasers, but as technology evolves violet and ultra-violet light lasers are expected to decrease in size and price.

Figure 8:
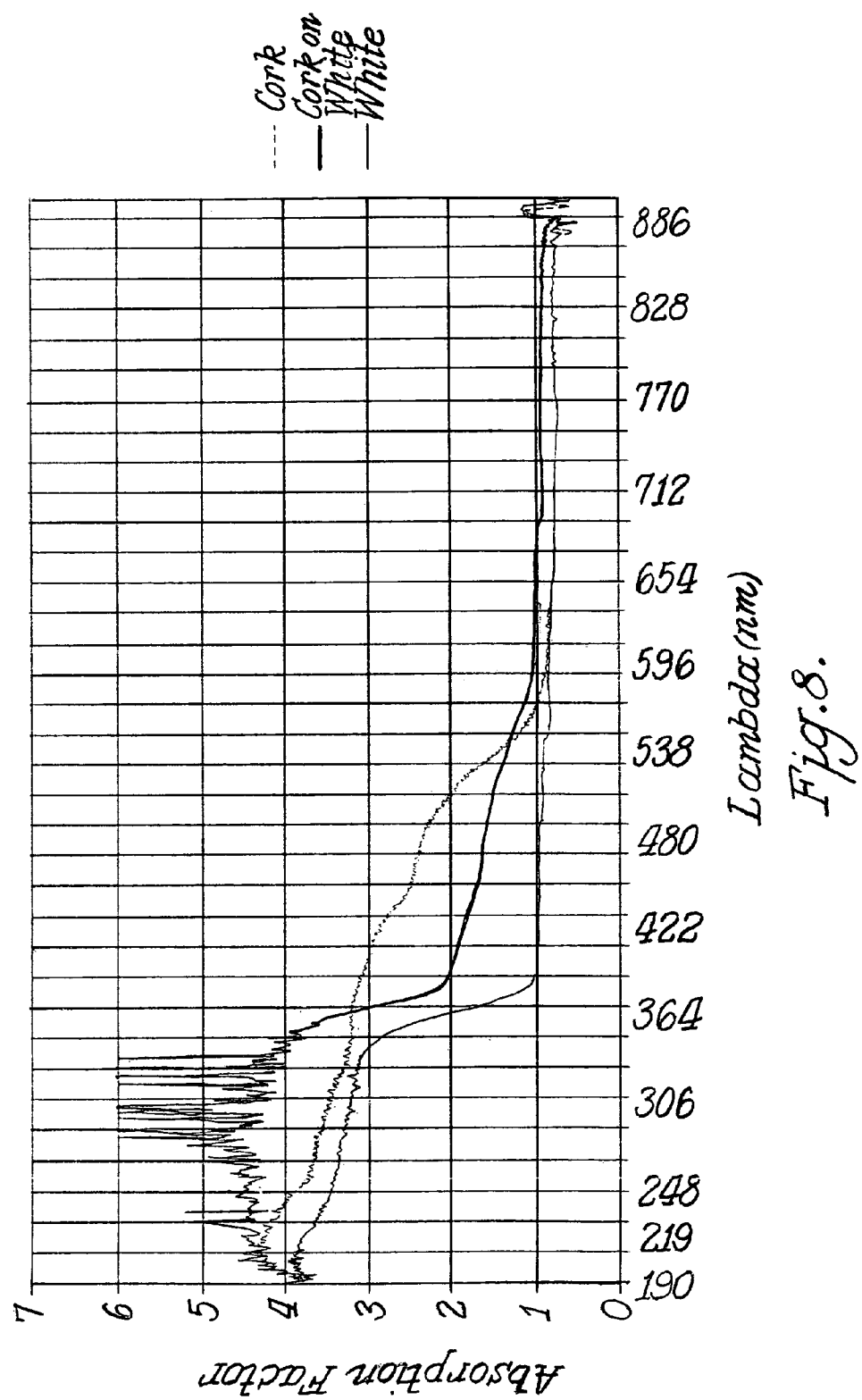
FIG. 8 is a graph showing how tipping paper absorption changes with the wavelength of the light source scanning the tipping paper.

The utility of using a violet or ultra-violet light laser as light source 12 is best seen in FIG. 8. As shown in FIG. 8, the paper absorption factor of tipping paper 100 is very small, but different for white, cork, and cork-on-white tipping paper. Therefore the stray light component will be different for different color tipping papers. However, decreasing the wavelength towards the ultra-violet, the paper absorption factor increases considerably so that around 350 nm the stray light component is expected to be negligible, leading to more accurate measurement resulting from a high signal-to-noise ratio. The use of violet or ultra-violet light for this purpose is not limited to use with lasers, but rather is applicable to any light source, including conventional halogen-based light sources.

FIG. 3 shows the narrow line of light 14 produced by light source 12, as compared to the large illumination area 106 produced by conventional light source 104. The exemplary dimensions of the narrow line of light 14, as shown in FIG. 3, are approximately 0.1 mm (or 100 microns) wide and approximately ten mm long. Although the dimensions of the narrow line of light 14 shown in FIG. 3 are preferred for tipping paper 100 having a low permeability of 50 to 500 Coresta units (smaller holes) and having a high permeability of 500 to 2500 Coresta units (larger holes), the dimensions of narrow line of light 14 are in no way limited to these values. Rather, the dimensions of narrow line of light 14 may vary depending upon the application of system 10A or 10B. Narrow line of light 14 may be produced with special optics inserted in front the laser, rather than by limiting the light field with a physical aperture. As further shown in FIG. 3, the total illuminated area of narrow line of light 14 is approximately two orders of magnitude smaller than the illuminated area of the traditional light source 104 (as represented by circle 106). This permits a very fine scanning of tipping paper 100, which improves the resolution and quality of system 10A or 10B over the conventional light permeability measuring system.

C. Skipping Detection

As shown in FIGS. 4 and 5, the system 10A or 10B of the present invention may be used to detect skipped (or missing) perforations 102 down to the level of a single missing perforation 102. FIG. 4 shows narrow line of light 14 scanning a tipping paper 100 that is not missing any perforations 102, whereas FIG. 5 shows narrow line of light 14 scanning a tipping paper 100 that is missing one perforation 102, wherein the missing perforation 102 is indicated by reference numeral 112. The signal generated by system 10A or 10B when used to scan the tipping paper 100 shown in FIG. 5 will be one half of the signal generated by system 10A or 10B when used to scan the tipping paper 100 shown in FIG. 4 because the total area of the tipping paper allowing light to pass through (i.e., the perforations 102) has been reduced in half. This approach is particularly efficient for tipping papers with one single row of perforations.

The direct digital pre-processing of optical signals allows inspection of very small portions of tipping paper 100, hereinafter referred to as "segments" and "sub-segments", at speeds up to 1500 meters per minute. The concept and capability of measuring defined length segments and sub-segments combined with fast processing of the data signals is instrumental for detecting skipped perforations (or missing holes) in tipping paper 100.

D. Alternative Optical Arrangements

As shown in FIGS. 6A, 6B, 7A, and 7B, system 10A or 10B of the present invention may have two different optical arrangements. FIGS. 6A and 6B show a first arrangement with an angled (or tilted) stray light sensor, and FIGS. 7A and 7B show a second arrangement with a polarized beam splitter and a straight stray light sensor. Each optical arrangement will be described in turn.

FIG. 6A shows the path of direct light in the first optical arrangement, whereas FIG. 6B shows the path of stray light in the first optical arrangement. As shown in these Figs., the first optical arrangement includes light source 12 that generates light through line forming optics 20 to create narrow line of light 14. Line of light 14 illuminates tipping paper 100, and direct light 22 travels through perforation 102 and enters light detector 18 through an aperture 23. Light detector 18 further includes: a stray light sensor 24 for measuring stray light; an optical beam collimating lens 26 for focusing direct light 22; a polarization filter 28 for filtering out stray light; a stray light filter 30 having an aperture 31 that further filters out stray light; and a direct light sensor 32 for sensing direct light 22. Direct light 22 enters light detector 18 through aperture 23, bypasses stray light sensor 24 due to aperture 23, is focused by optical lens 26, travels through polarization filter 28 and aperture 31, and is sensed by direct light sensor 32. Polarizing filter 28 filters out stray light, but allows direct light 22 to pass through, enhancing the separation between direct light 22 and the stray light by increasing the signal-to-noise ratio.

FIG. 6B is identical to FIG. 6A, except that FIG. 6B shows the path of stray light 34 as it travels through tipping paper 100. Although most of the stray light 34 fails to enter light detector 18, some stray light 34 does enter light detector 18 through aperture 23. It is not desirous to have stray light 34 enter direct light sensor 32. As shown in FIG. 6B, the first optical arrangement prevents stray light 34 from being detected by direct light sensor 32. Stray light 34 is prevented from being detected by direct light sensor 32 because first, the polarization filter 28 reduces those components of stray light 34 with different polarization than direct light 22, and then aperture 31 reduces the components with the same polarization as direct light 22. In addition, the different focusing distances for direct light 22 and stray light 34 prevents stray light 34 from being detected by direct light sensor 32. Direct light 22 is generated at a distance $g_1$ from optical lens 26, allowing the re-collimated direct light 22 to focus on direct light sensor 32 at a distance $h_1$. At the same time, the stray light 34 is generated at the tipping paper 100 at a distance $g_2$ (which equals the focal distance f of optical lens 26). This arrangement causes the re-collimated stray light 34 to focus beyond direct light sensor 32, at a distance $h_2$. Calculating mathematically using the following optical equations:

$$\frac{1}{f} = \frac{1}{g_1} + \frac{1}{h_1} = \frac{1}{g_2} + \frac{1}{h_2},$$

and solving for distance $h_2$ provides:

$$h_2 = \frac{g_2 * f}{g_2 - f}.$$

Thus, as distance $g_2$ approaches the focal distance f, then distance $h_2$ approaches infinity. At the same time, aperture 23 and the angled position of stray light sensor 24 prevent direct light 22 from reaching stray light sensor 24. The stray light signal generated by stray light sensor 24 may be used to identify changes in the transmissive property of tipping paper 100 that may be created by variations in tipping paper color intensity or thickness, so as to detect changes in the basis weight and allow these variations to be removed from the signal generated by direct light sensor 32 through software (see the calibration equation discussed below).

FIG. 7A shows the path of direct light in the second optical arrangement, whereas FIG. 7B shows the path of stray light in the second optical arrangement. As shown in these Figs., the second optical arrangement is identical to the first optical arrangement shown in FIGS. 6A and 6B, except the angled stray light sensor 24 is not angled in the second optical arrangement shown in FIGS. 7A and 7B. Rather, a polarized beam splitter 36 is provided and stray light sensor 24 is aligned with polarized beam splitter 36. Such a configuration eliminates the need for precise angle mounting of stray light sensor 24, improves the reproducibility of the optical arrangement, and improves the consistency of the sensor performance. Polarized beam splitter 36 directs most of the stray light 34 toward stray light sensor 34, and the residual stray light 34 (having the same polarization as direct light 22) is prevented from reaching direct light sensor 32 by optical lens 26 and aperture 31. Another difference in the second optical arrangement is that polarization filter 28 is not used. Instead, a polarization filter 38 is provided between polarized beam splitter 36 and stray light sensor 24 to help remove residual, reflected components of direct light 22 from the stray light 34 entering stray light sensor 24. Thus, the second optical arrangement separates the direct light from the stray light even more efficiently than the first optical arrangement.

E. Dithering

Dithering of light source 12 may be used to minimize the effect of inherent differential non-linearity of the light intensity by averaging the intensity values across the narrow line of light 14. The light intensity across the narrow line of light 14 usually has variations. Such variations are called "integral non-linearity" for the entire ten millimeter length of the narrow line of light 14. Variations are called "differential non-linearity" for contiguous small segments of the ten millimeter length.

Figure 9:
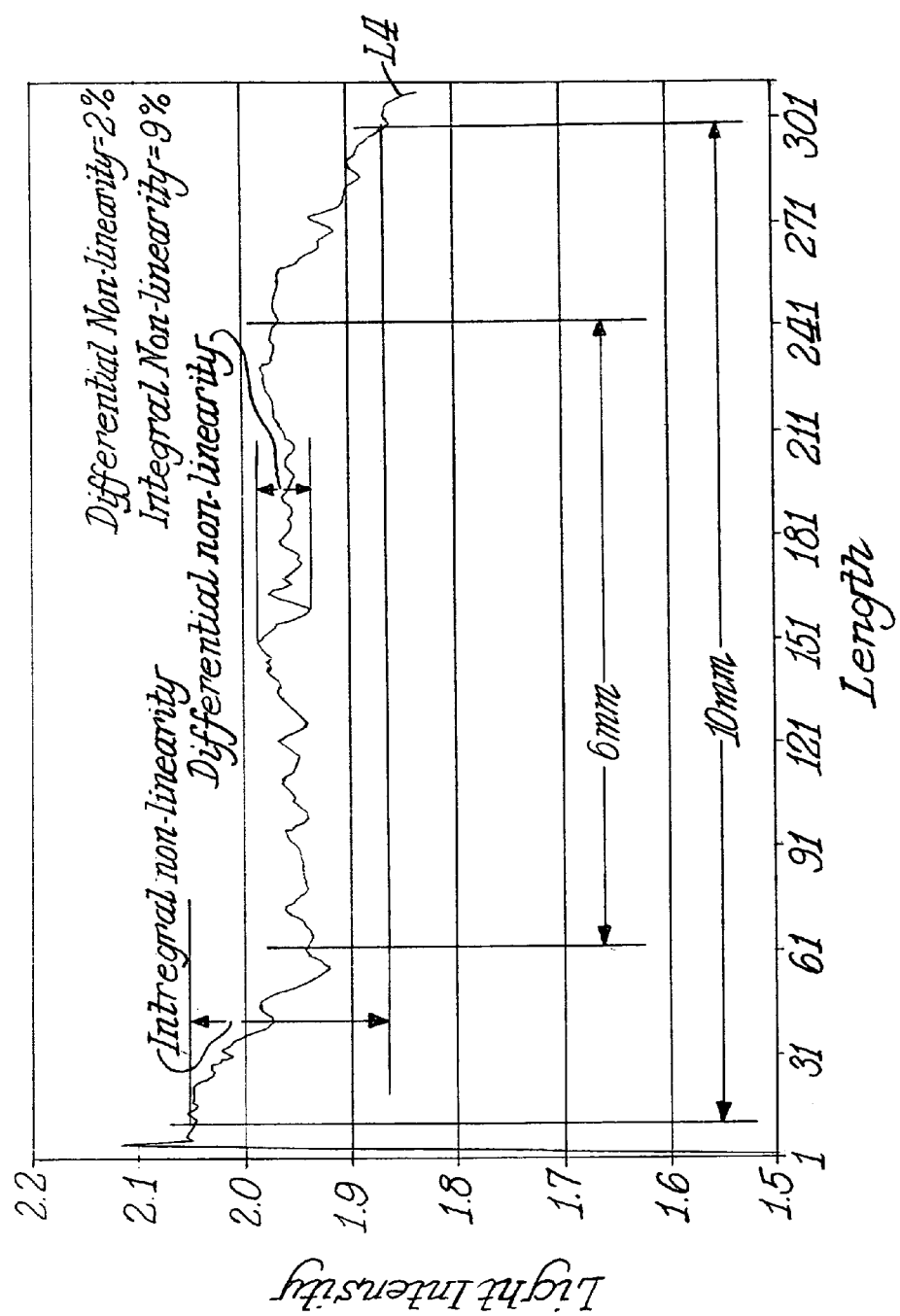
FIG. 9 is a graph showing the light intensity of a light source of the system shown in FIGS. 2A and 2B.
Figure 10:
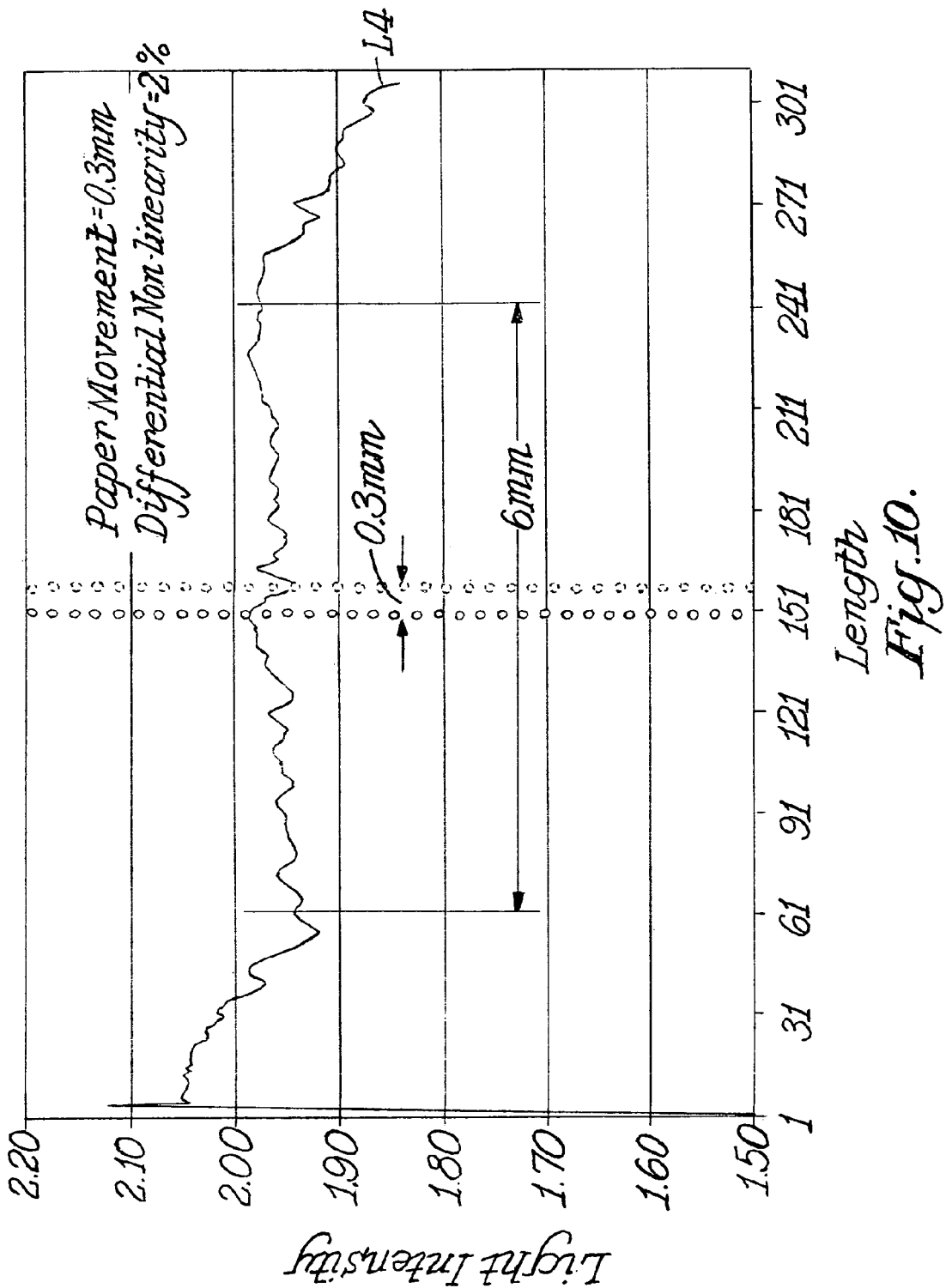
FIG. 10 is a graph showing the measurement error due to perforation movement of the tipping paper.
Figure 11:
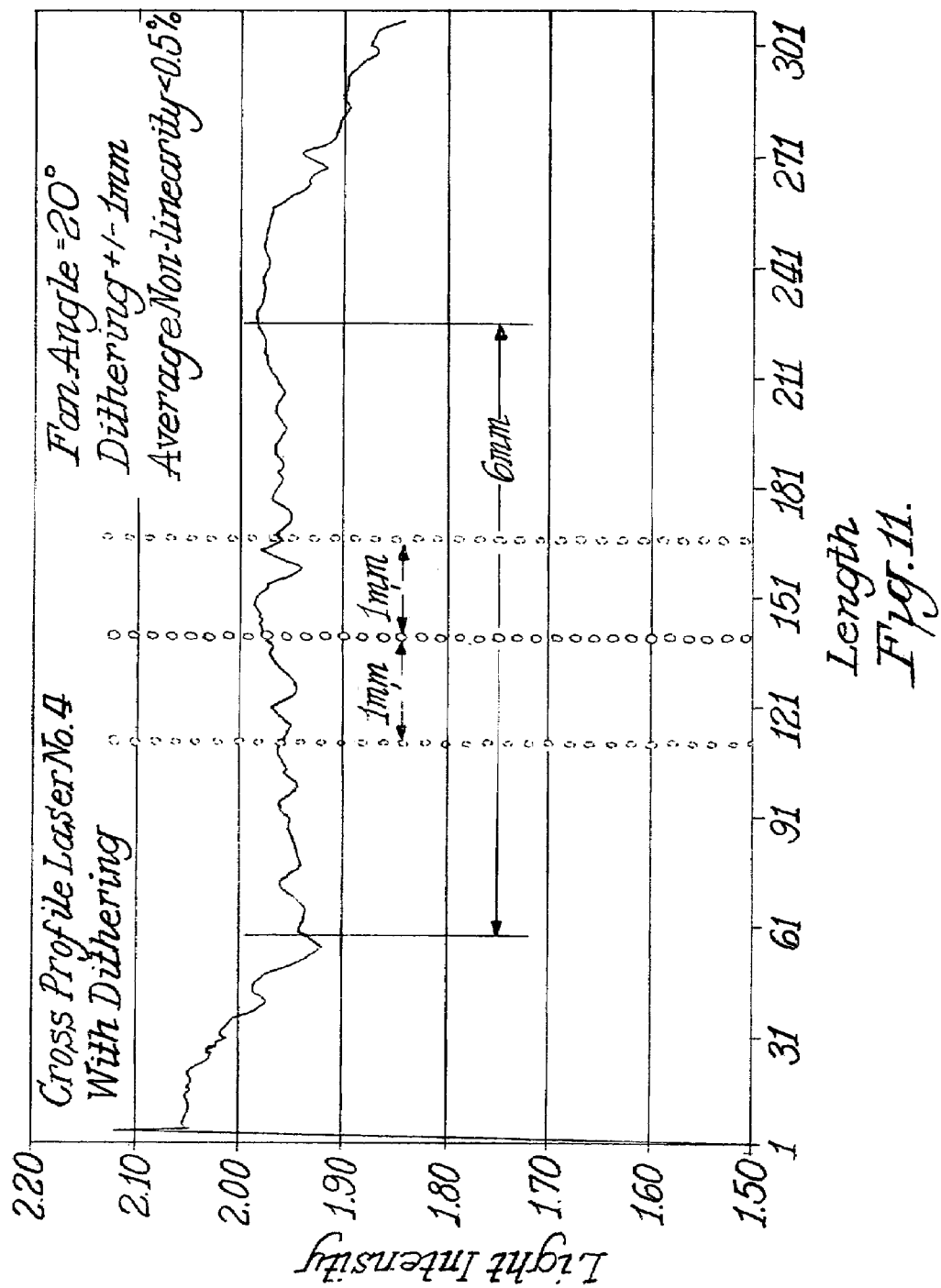
FIG. 11 is a graph showing how the system of the present invention, as shown in FIGS. 2A and 2B, reduces the measurement error shown in FIG. 10 with dithering.

A typical cross profile of a laser light source intensity across the narrow line of light 14 is shown in FIG. 9, with an integral non-linearity of 9% and a differential non-linearity of 2%. If one considers only a six millimeter length of the line of light 14 (it is assumed that that a maximum of six rows of perforations 102 will encompass six millimeters), the differential non-linearity will be 2%. This means that the measuring error for tipping paper 100 having a single row of perforations could be as high as 2% if the position of the holes changes by 0.3 mm, as shown in FIG. 10. In order to reduce this error, laser light source 12 may be moved alternately left to right within ±1 mm from the center position, resulting in an average repeatability error of less than 0.5%, as shown in FIG. 11. The signal component resulting from the oscillating movement may be digitally filtered out. Such dithering may be accomplished in a number of ways, including mechanically with a mechanism using a servo motor, electrically with a piezoelectric crystal attached to light source 12, etc. The dithering principle may be applied to any light source used for measuring tipping paper permeability, and may be extended to measuring other properties of different materials using light scanning. Dithering of light source 12 may be efficient for tipping paper winding systems with very stable lateral movement. For less stable systems in which the paper moves sideways randomly and continuously, the paper movement has the same effect as the light source dithering, so the light source 12 may remain in a fixed position without any dithering movement.

F. Calibration Of The System

System 10A or 10B of the present invention may be calibrated with the calibration targets (or standards) disclosed in co-pending U.S. patent application Serial No. 10/854,438, assigned to the assignee of the present invention, Philip Morris USA, Inc., the entire disclosure of which being incorporated by reference herein.

G. Signal Processing

Figure 12:
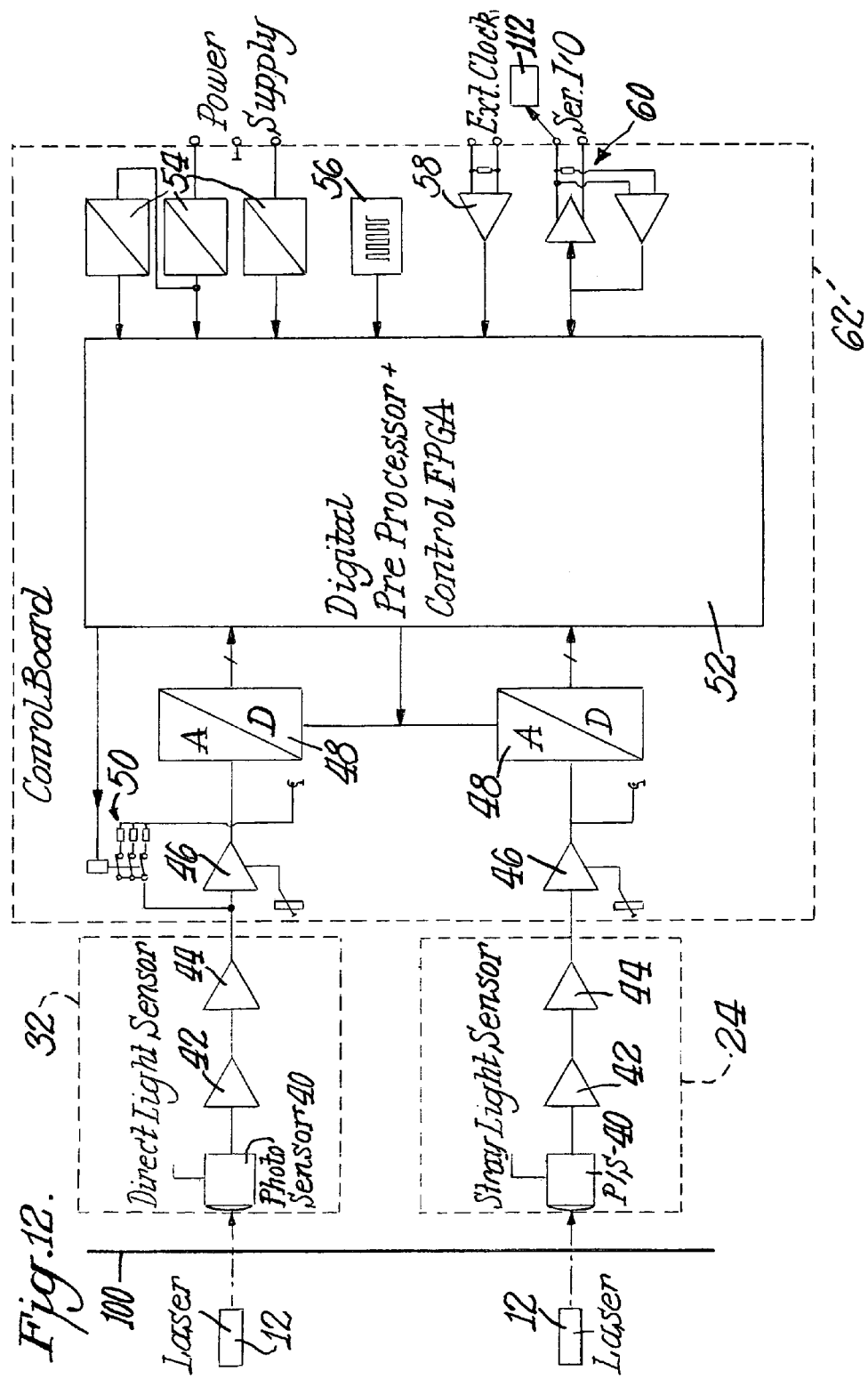
FIG. 12 is a schematic electrical circuit diagram showing the electrical components of the system shown in FIGS. 2A and 2B.

FIG. 12 is an electrical schematic showing the details of direct light sensor 32 and stray light sensor 24, as shown in FIGS. 6A, 6B, 7A, and 7B, and how they interact with a digital processing device such as a control board 62. Control board 62 may be housed within light sensor 18, but may also be external to light sensor 18. In one aspect of the present invention, a smart digital light sensor is used for light sensor 18 for measuring light passing through perforations 102 of tipping paper 100. Such a smart digital light sensor includes an integrated digitizer and digital signal pre-processing ("DSP") for fast interpretation of signals generated by direct light sensor 32 and stray light sensor 24. A smart digital light sensor does not need any physical adjustment related to brand changes or measuring range, whereas conventional analog sensors require several analog adjustments (e.g., potentiometers).

As shown in FIG. 12, the light from light source 12 is received by direct light sensor 32 and stray light sensor 24 and converted into an analog electrical signal with a photo sensor 40. The analog electrical signal is then amplified with amplifiers 42, 44, 46, and converted into a digital electrical signal with an analog-to-digital ("A/D") converter or integrated digitizer 48. One A/D converter 48 cooperates with a gain control 50. The digital electrical signals are then provided to a digital pre-processor and control FPGA (field programmable gate array) 52 where they are pre-processed and output, via a serial input/output port 60, to a computing device 112 for storage or further processing. Control board 62 further includes a power supply 54 (made up of three regulators/filters), an internal clock 56, and an external clock 58.

Computing device 112 represents a combination of hardware and software, and thus may comprise a conventionally programmed computer, a programmed logic controller ("PLC"), a microcontroller embedded with software, or any other intelligent system. Computing device 112 may be used in place or in conjunction with digital pre-processor and control FPGA 52. Further, computing device 112 may not be used at all if digital pre-processor and control FPGA 52 includes at least a memory device.

Figure 13:
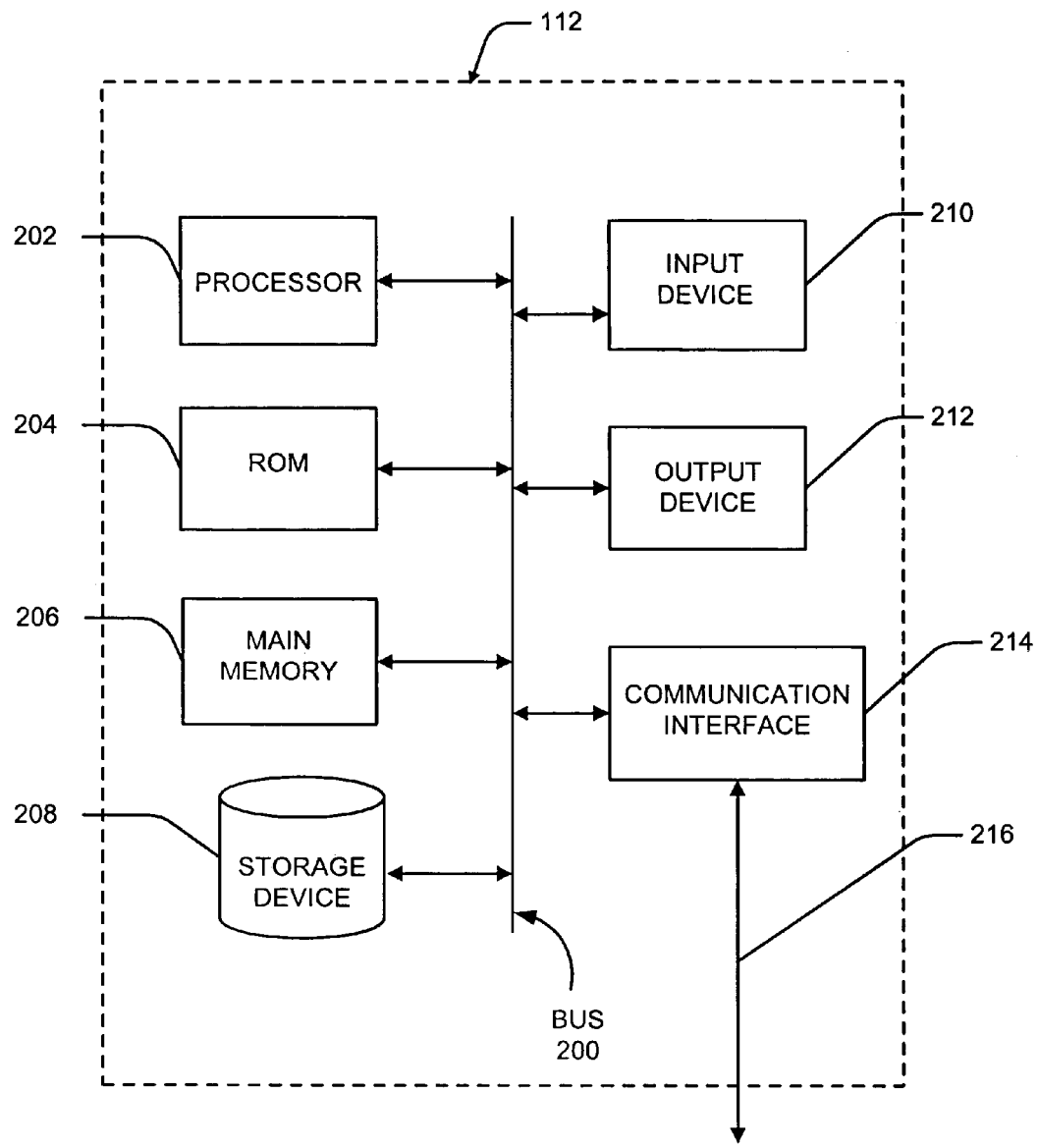
FIG. 13 is a schematic diagram showing a computing device capable of use with the system of the present invention as shown in FIGS. 2A and 2B.

Referring to FIG. 13, if computing device 112 is a conventionally programmed computer, then such a computer may include a bus 200 interconnecting a processor 202, a read-only memory (ROM) 204, a main memory 206, a storage device 208, an input device 210, an output device 212, and a communication interface 214. Bus 200 is a network topology or circuit arrangement in which all devices are attached to a line directly and all signals pass through each of the devices. Each device has a unique identity and can recognize those signals intended for it. Processor 202 includes the logic circuitry that responds to and processes the basic instructions that the drive computer. ROM 204 includes a static memory that stores instructions and data used by processor 202.

Computer storage is the holding of data in an electromagnetic form for access by a computer processor. Main memory 206, which may be a RAM or another type of dynamic memory, makes up the primary storage of the computer. Secondary storage of the computer may comprise storage device 208, such as hard disks, tapes, diskettes, Zip drives, RAID systems, holographic storage, optical storage, CD-ROMs, magnetic tapes, and other external devices and their corresponding drives. Main memory 206 and/or storage device 208 may store any of the data retrieved from any of the components of the present invention.

Input device 210 may include a keyboard, mouse, pointing device, sound device (e.g. a microphone, etc.), biometric device, or any other device providing input to the computer. Output device 212 may comprise a display, a printer, a sound device (e.g. a speaker, etc.), or other device providing output to the computer. Communication interface 214 may include network connections, modems, or other devices used for communications with other computer systems or devices.

Communication links 216 may be wired, wireless, optical or a similar connection mechanisms. "Wireless" refers to a communications, monitoring, or control system in which electromagnetic or acoustic waves carry a signal through atmospheric space rather than along a wire. In most wireless systems, radio-frequency (RF) or infrared (IR) waves are used. Some monitoring devices, such as intrusion alarms, employ acoustic waves at frequencies above the range of human hearing.

Computing device 112 consistent with the present invention may perform the tasks of receiving digital signals from control board 62 and storing the signals or producing an output that is the light permeability equivalent of the air permeability of tipping paper 100 from the signals generated by direct light sensor 32 and stray light sensor 24, using the measuring algorithm discussed below. However, control board 62 may perform these tasks on its own as well. Computing device 110 may perform these tasks in response to a processor executing sequences of instructions contained in a computer-readable medium. A computer-readable medium may include one or more memory devices and/or carrier waves.

Execution of the sequences of instructions contained in a computer-readable medium causes the processor to perform the processes described below. Alternatively, hardwired circuitry may be used in place of or in combination with software instructions to implement processes consistent with the present invention. Thus, the present invention is not limited to any specific combination of hardware circuitry and software.

In order to calculate the equivalent air permeability of tipping paper 100 from the signals generated by direct light sensor 32 and stray light sensor 24, the measuring algorithm uses specific parameters determined during system calibration. The calibration curve slope $C_{slope}$ and intercept $C_{int}$, as described in co-pending U.S. patent application Serial No. 10/854,438, are calculated during calibration. The algorithm used during calibration is tailored to the specific configuration of the sensor being calibrated. If the sensor configuration changes, then the algorithm will change as well. For example, a calibration equation which defines the correlation between light permeability and air permeability may be created by measuring two different, previously certified targets with an air-flow measuring instrument and a light measuring instrument. These measurements provide first and second air permeabilities $AP_1$ and $AP_2$ which correlate with first and second light permeabilities $LP_1$ and $LP_2$. These values enable the calibration parameters of the calibration equation to be calculated, namely the slope $C_{slope}$ and the intercept $C_{int}$ of the equation. The calibration equation will thus be $AP = C_{slope} \times LP + C_{int}$, where:

$$C_{slope} = \frac{AP_2 - AP_1}{LP_2 - LP_1}, \text{ and } C_{int} = \frac{LP_2 \times AP_1 - LP_1 \times AP_2}{LP_2 - LP_1}.$$

The calibration equation defines the correlation between light permeability and air permeability, which can be considered linear for a limited range of permeability values. Once the slope $C_{slope}$ and intercept $C_{int}$ are calculated, the light permeability of a material may be measured, and based upon the calibration equation the equivalent air permeability (AP) of the material may be calculated. Another parameter used in the calculation is called the paper factor (PF), which is the ratio between the signals generated by stray light sensor 24 and direct light sensor 32 as measured with non-perforated paper. The paper factor (PF) permits correction of the impact that the residual stray light on direct light sensor 32, and helps determine inherent variations of the paper basis weight. The equations used to calculate the paper factor (PF) and permeability (P) are:

$$PF = \frac{AD_{direct}}{AD_{stray}},$$

and $$P = \int \{C_{slope} \times [(AD_{direct} - O_{direct}) - PF \times (AD_{stray} - O_{stray})] + C_{int}\},$$

where $C_{slope}$ is the slope of the calibration curve, $C_{int}$ is the intercept of the calibration curve, $AD_{direct}$ represents the analog-to-digital (A/D) counts measured by direct light sensor 32, $O_{direct}$ is the offset of direct light sensor 32, $AD_{stray}$ represents the A/D counts measured by stray light sensor 24, $O_{stray}$ is the offset of stray light sensor 24, and PF is the paper factor. The offsets ($O_{direct}$, $O_{stray}$) represent residual currents of sensors 24, 32 with light source 18 turned off.

H. Speed Independent Measurement

The permeability measurement by system 10A or 10B of the present invention is independent of the tipping paper velocity since the data is collected at sampling intervals determined by pulses generated with a shaft encoder (which is the external clock 58 shown in FIG. 12) installed on the rewinding drum of the tipping paper machine, which moves in synch with the tipping paper.

I. Automatic Correction Of Calibration Parameters

Accuracy of system 10A or 10B of the present invention may deteriorate over time due to aging of light source 12, light sensor offset variations due to temperature changes, dust accumulation on the optical components, etc. In order to keep system 10A or 10B operating at maximum performance, a measurement of the light transmission through a very fine aperture (inserted in between the light source and light sensor, like a piece of paper, but in a very stable and mechanically repeatable position) may be used to compare the entire light transmission capability of the measuring head. A first measurement may be performed during system 10A or 10B installation, and then performed periodically (e.g., once per shift or before each bobbin run). A deviation larger than a predetermined amount would require application of a correction to the original values of either the slope $C_{slope}$ or the intercept $C_{int}$ parameter of the calibration curve, which restores the original transmission characteristics of the measuring channel.

It will be apparent to those skilled in the art that various modifications and variations can be made in the calibration system and target of the present invention and in construction of the system and target without departing from the scope or spirit of the invention. Examples of such modifications have been previously provided.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A system for measuring the permeability of a material, the system comprising:
   a light source for illuminating the material;
   a stray light sensor for detecting stray light traveling through the material from the light source and outputting a stray light signal indicative of the stray light detected;
   a direct light sensor for detecting direct light traveling through at least one hole provided in the material from the light source and outputting a direct light signal indicative of the direct light detected; and
   a digital processing device for receiving the stray light and direct light signals and calculating the permeability of the material.

2. A system for measuring the permeability of a material, as recited in claim 1, wherein the light source comprises a polarized light source, the direct light has the same polarization as the light source, and the stray light has a different polarization than the light source.

3. A system for measuring the permeability of a material, as recited in claim 1, wherein the light source comprises a coherent modulated or non-modulated light source.

4. A system for measuring the permeability of a material, as recited in claim 1, wherein the light source comprises a red laser light source.

5. A system for measuring the permeability of a material, as recited in claim 4, wherein the light source further comprises an ultraviolet light source.

6. A system for measuring the permeability of a material, as recited in claim 5, wherein the ultraviolet light source reduces the detected stray light irregardless of the color of the material.

7. A system for measuring the permeability of a material, as recited in claim 1, wherein the light source produces a narrow line of light.

8. A system for measuring the permeability of a material, as recited in claim 7, wherein the narrow line of light is approximately 0.1 millimeters wide by 10 millimeters long.

9. A system for measuring the permeability of a material, as recited in claim 7, wherein the narrow line of light is capable of detecting a single missing perforation in the material.

10. A system for measuring the permeability of a material, as recited in claim 1, further comprising:
    a polarization filter, provided between the light source and the direct light sensor, for preventing the stray light from entering the direct light sensor.

11. A system for measuring the permeability of a material, as recited in claim 1, wherein the stray light sensor is provided at an angle to the direction of the direct light.

12. A system for measuring the permeability of a material, as recited in claim 11, further comprising:
    an optical beam collimating lens provided between the light source and the direct light sensor for re-collimating the direct light onto the surface of the direct light sensor and for re-collimating the stray light beyond the surface of the direct light sensor.

13. A system for measuring the permeability of a material, as recited in claim 11, further comprising:
    an aperture provided between the light source and the direct light sensor, wherein the aperture and angled position of the stray light sensor prevent the direct light from reaching the stray light sensor.

14. A system for measuring the permeability of a material, as recited in claim 1, wherein the stray light sensor is provided at an angle perpendicular to the direction of the direct light.

15. A system for measuring the permeability of a material, as recited in claim 14, further comprising:
    a polarized beam splitter provided between the light source and the stray light sensor for separating the stray light from the direct light.

16. A system for measuring the permeability of a material, as recited in claim 15, further comprising:
    a polarization filter, provided between the polarized beam splitter and the stray light sensor, for preventing the direct light from entering the stray light sensor.

17. A system for measuring the permeability of a material, as recited in claim 14, further comprising:
    an optical beam collimating lens provided between the light source and the direct light sensor for re-collimating the direct light onto the surface of the direct light sensor and for re-collimating the stray light beyond the surface of the direct light sensor.

18. A system for measuring the permeability of a material, as recited in claim 14, further comprising:
    an aperture provided between the light source and the direct light sensor, wherein the aperture prevents the direct light from reaching the stray light sensor.

19. A system for measuring the permeability of a material, as recited in claim 1, wherein the light source is dithered to minimize the effect of inherent differential non-linearity of the light intensity.

20. A system for measuring the permeability of a material, as recited in claim 19, wherein the light source is dithered mechanically or electrically.

21. A system for measuring the permeability of a material, as recited in claim 1, wherein the digital processing device comprises an integrated digitizer and digital signal pre-processing device.

22. A system for measuring the permeability of a material, as recited in claim 1, wherein the digital processing device calculates the permeability (P) of the material from the stray light and direct light signals using the following equation:

$$P=\int\{C_{slope}\times[(AD_{direct}-O_{direct})-PF\times(AD_{stray}-O_{stray})]+C_{int}\},$$

where $C_{slope}$ is the slope of a calibration curve, $C_{int}$ is the intercept of a calibration curve, $AD_{direct}$ is the direct light signal, $O_{direct}$ is an offset of the direct light sensor, $AD_{stray}$ is the stray light signal, $O_{stray}$ is an offset of the stray light sensor, and PF is a factor dependant upon the material.

23. A system for measuring the permeability of a material, as recited in claim 22, wherein the material-dependent factor PF is calculated by the digital processing device using the following equation:

$$PF = \frac{AD_{direct}}{AD_{stray}}.$$

24. A system for measuring the permeability of a material, as recited in claim 1, wherein the digital processing device comprises:
 a computer memory for storing the stray light and direct light signals; and
 a computer processor for calculating the permeability (P) of the material from the stray light and direct light signals stored in the computer memory, wherein the computer processor is electrically coupled to the computer memory.

25. A system for measuring the permeability of a material, as recited in claim 24, wherein the computer processor calculates the permeability (P) of the material from the stray light and direct light signals using the following equation:

$$P=\int\{C_{slope}\times[(AD_{direct}-O_{direct})-PF\times(AD_{stray}-O_{stray})]+C_{int}\},$$

where $C_{slope}$ is the slope of a calibration curve, $C_{int}$ is the intercept of a calibration curve, $AD_{direct}$ is the direct light signal, $O_{direct}$ is an offset of the direct light sensor, $AD_{stray}$ is the stray light signal, $O_{stray}$ is an offset of the stray light sensor, and PF is a factor dependant upon the material.

26. A system for measuring the permeability of a material, as recited in claim 25, wherein the material-dependent factor PF is calculated by the computer processor using the following equation:

$$PF = \frac{AD_{direct}}{AD_{stray}}.$$

27. A system for measuring the permeability of a material, as recited in claim 1, wherein the material comprises tipping paper.

28. A system for measuring the permeability of a material, as recited in claim 1, wherein the permeability measurement of the material is independent of a velocity of the material.

29. A method for measuring the permeability of a material, the method comprising:
 illuminating the material with a light source;
 detecting stray light traveling through the material from the light source and outputting a stray light signal indicative of the stray light detected with a stray light sensor;
 detecting direct light traveling through at least one hole provided in the material from the light source and outputting a direct light signal indicative of the direct light detected with a direct light sensor; and
 receiving the stray light and direct light signals and calculating the permeability of the material with a digital processing device.

30. A method for measuring the permeability of a material, as recited in claim 29, wherein the illuminating step comprises producing a narrow line of light with the light source.

31. A method for measuring the permeability of a material, as recited in claim 29, further comprising:
 preventing the stray light from entering the direct light sensor with a polarization filter provided between the light source and the direct light sensor.

32. A method for measuring the permeability of a material, as recited in claim 29, further comprising:
 re-collimating the direct light onto the surface of the direct light sensor and re-collimating the stray light beyond the surface of the direct light sensor with an optical beam collimating lens provided between the light source and the direct light sensor.

33. A method for measuring the permeability of a material, as recited in claim 29, further comprising:
 preventing the direct light from reaching the stray light sensor with an aperture provided between the light source and the direct light sensor, and by positioning the stray light sensor at an angle to the direction of the direct light.

34. A method for measuring the permeability of a material, as recited in claim 29, further comprising:
 separating the stray light from the direct light with a polarized beam splitter provided between the light source and the stray light sensor.

35. A method for measuring the permeability of a material, as recited in claim 34, further comprising:
 preventing the direct light from entering the stray light sensor with a polarization filter provided between the polarized beam splitter and the stray light sensor.

36. A method for measuring the permeability of a material, as recited in claim 34, further comprising:
 re-collimating the direct light onto the surface of the direct light sensor and re-collimating the stray light beyond the surface of the direct light sensor with an optical beam collimating lens provided between the light source and the direct light sensor.

37. A method for measuring the permeability of a material, as recited in claim 34, further comprising:
 preventing the direct light from reaching the stray light sensor with an aperture provided between the light source and the direct light sensor.

38. A method for measuring the permeability of a material, as recited in claim 29, further comprising:
 dithering the light source to minimize the effect of inherent differential non-linearity of the light intensity.

39. A method for measuring the permeability of a material, as recited in claim 29, wherein the digital processing device calculates the permeability (P) of the material from the stray light and direct light signals using the following equation:

$$P=\int\{C_{slope}\times[(AD_{direct}-O_{direct})-PF\times(AD_{stray}-O_{stray})]+C_{int}\},$$

where $C_{slope}$ is the slope of a calibration curve, $C_{int}$ is the intercept of a calibration curve, $AD_{direct}$ is the direct light signal, $O_{direct}$ is an offset of the direct light sensor, $AD_{stray}$ is the stray light signal, $O_{stray}$ is an offset of the stray light sensor, and PF is a factor dependant upon the material.

40. A method for measuring the permeability of a material, as recited in claim 39, wherein the material-dependent factor PF is calculated by the digital processing device using the following equation:

$$PF = \frac{AD_{direct}}{AD_{stray}}.$$

41. A method for measuring the permeability of a material, as recited in claim 29, further comprising:
    storing the stray light and direct light signals with a computer memory; and
    calculating the permeability (P) of the material from the stray light and direct light signals stored in the computer memory with a computer processor, wherein the computer processor is electrically coupled to the computer memory.

42. A method for measuring the permeability of a material, as recited in claim 41, wherein the computer processor calculates the permeability (P) of the material from the stray light and direct light signals using the following equation:

$$P = \int \{C_{slope} \times [(AD_{direct} - O_{direct}) - PF \times (AD_{stray} O_{stray})] + C_{int}\},$$

where $C_{slope}$ is the slope of a calibration curve, $C_{int}$ is the intercept of a calibration curve, $AD_{direct}$ is the direct light signal, $O_{direct}$ is an offset of the direct light sensor, $AD_{stray}$ is the stray light signal, $O_{stray}$ is an offset of the stray light sensor, and PF is a factor dependant upon the material.

43. A method for measuring the permeability of a material, as recited in claim 42, wherein the material-dependent factor (PF) is calculated by the computer processor using the following equation:

$$PF = \frac{AD_{direct}}{AD_{stray}}.$$

44. A method for measuring the permeability of a material, as recited in claim 29, wherein the material comprises tipping paper.

45. A method for measuring the permeability of a material, as recited in claim 29, wherein the permeability measurement of the material is independent of a velocity of the material.

46. A system for measuring the permeability of a tipping paper, the system comprising:
    a laser light source for illuminating the material with a narrow line of light;
    a stray light sensor for detecting stray light traveling through the tipping paper from the laser light source and outputting a stray light signal indicative of the stray light detected;
    a direct light sensor for detecting direct light traveling through at least one hole provided in the tipping paper from the laser light source and outputting a direct light signal indicative of the direct light detected; and
    a digital processing device for receiving the stray light and direct light signals and calculating the permeability (P) of the tipping paper from the stray light and direct light signals using the following equation:

$$P = \int \{C_{slope} \times [(AD_{direct} - O_{direct}) - PF \times (AD_{stray} - O_{stray})] + C_{int}\},$$

where $C_{slope}$ is the slope of a calibration curve, $C_{int}$ is the intercept of a calibration curve, $AD_{direct}$ is the direct light signal, $O_{direct}$ is an offset of the direct light sensor, $AD_{stray}$ is the stray light signal, $O_{stray}$ is an offset of the stray light sensor, and PF is a paper factor, wherein the paper factor (PF) is calculated by the digital processing device using the following equation:

$$PF = \frac{AD_{direct}}{AD_{stray}}.$$

* * * * *